United States Patent [19]

Pader

[11] 4,364,837

[45] Dec. 21, 1982

[54] SHAMPOO COMPOSITIONS COMPRISING SACCHARIDES

[75] Inventor: Morton Pader, Teaneck, N.J.

[73] Assignee: Lever Brothers Company, New York, N.Y.

[21] Appl. No.: 300,078

[22] Filed: Sep. 8, 1981

[51] Int. Cl.$^3$ .............................................. C11D 3/22
[52] U.S. Cl. .................................. 252/173; 252/89.1; 252/174.15; 252/174.17; 252/174.23; 252/DIG. 4; 252/DIG. 13; 424/70
[58] Field of Search ............. 424/70; 252/173, 174.15, 252/174.17, 174.23, 89.1, DIG. 4, DIG. 13

[56] References Cited

U.S. PATENT DOCUMENTS

| | | |
|---|---|---|
| 2,237,629 | 1/1941 | Orelup . |
| 2,826,551 | 3/1958 | Geen . |
| 3,149,042 | 9/1964 | Habicht et al. . |
| 3,533,955 | 10/1970 | Pader et al. . |
| 3,932,610 | 1/1976 | Rudy et al. . |
| 3,950,510 | 4/1976 | Adams . |
| 3,957,970 | 5/1976 | Korkis . |
| 3,964,500 | 6/1976 | Drakoff . |
| 3,988,438 | 10/1976 | Weinstein . |
| 3,998,761 | 12/1976 | Gary et al. . |
| 4,048,301 | 9/1977 | Popantoniou ......................... 424/70 |
| 4,061,602 | 12/1977 | Oberstar et al. .................... 252/547 |
| 4,087,518 | 5/1978 | Smith et al. . |

FOREIGN PATENT DOCUMENTS 1065730  11/1979  Canada ........................... 252/174.17

OTHER PUBLICATIONS

Todd et al, American Perfumer & Cosmetics, 86 112 (1971).

*Primary Examiner*—John E. Kittle
*Assistant Examiner*—Robert A. Wax
*Attorney, Agent, or Firm*—Irving N. Feit; James J. Farrell

[57] ABSTRACT

A freely pourable, substantially homogeneous shampoo composition with superior foaming properties and stability is disclosed.

The shampoo comprises:
(a) about 15 to about 70% by weight of a water-miscible saccharide;
(b) about 20 to about 75% by weight water;
(c) about 0.1 to about 30% by weight of at least one nonionic or cationic hair grooming agent; and
(d) about 3 to about 60% by weight of an anionic detergent;

and has a viscosity of about 400 to about 6,000 cps at 25° C.

55 Claims, No Drawings

SHAMPOO COMPOSITIONS COMPRISING SACCHARIDES

BACKGROUND OF THE INVENTION

The present invention is directed to freely pourable, homogeneous, water-based shampoos with enhanced stability and foam quality. More particularly, the invention is directed to shampoos containing detergents, hair grooming agents and saccharides.

The minimum function of a shampoo is to cleanse the hair. Cleansing is accomplished by removing natural oils, which are called sebum, and extraneous substances which accumulate from the atmosphere or are added intentionally, e.g., hair spray resins.

In order to cleanse the hair, shampoos generally contain a cleansing agent such as a detergent or soap. Detergents are preferable to soaps because of a detergent's ability to provide rich lather during use regardless of water hardness. A rich lather is advantageous because it enhances consumer perception of the shampoo and adds to its commercial acceptability.

It is also desirable for a shampoo to leave the hair in an improved condition for combing, to make the hair more manageable, to provide greater body and luster, to prevent fly-away, to minimize static electricity in the hair, to improve the tactile impression of the hair, and the like. These and other similar effects come under the general heading of hair conditioning.

In order to provide hair conditioning in addition to cleansing, a hair conditioning or grooming agent is advantageously added to shampoos. In order to function properly, the hair grooming agent must become deposited on the hair during the shampooing operation. In addition, it must remain deposited after the rest of the shampoo composition has been removed by rinsing the hair with water. It is the presence on the hair of the deposited hair grooming agent that provides the conditioning.

Consumers generally desire shampoos which are sold in the form of pourable, homogeneous liquids. Such shampoos are preferable to other forms because they are easier to dispense homogeneously onto the hair. Dispensing the shampoo homogeneously is especially important with those shampoos which contain hair grooming agents. If such shampoos are not dispensed homogeneously, the hair grooming agent will be unevenly applied to the hair and the hair will take on an uneven appearance.

One way to assure good deposition of the hair grooming agent from a freely pourable shampoo composition is to use a material which is homogeneously dispersed in the composition but which separates from the other ingredients when the composition is diluted with water during the shampooing process. For example, co-assigned U.S. Pat. No. 3,932,610 is directed to shampoo compositions which contain hair grooming agents made substantially soluble in an aqueous-based shampoo composition by properly selecting the solvent and/or solvent-surfactant system. Such hair grooming agents are generally insoluble in the amounts of water normally used in the shampooing and rinsing operations.

Homogeneous shampoos need not necessarily be actual solutions. Hair grooming agents or other ingredients may also be present in the form of colloidal dispersions or emulsions. If particles dispersed in a shampoo are too large to be considered colloidal, the shampoo may be in the form of a suspension of particles homogeneously dispersed in a liquid. Suspensions are normally not stable, however, unless the liquid is sufficiently viscous.

Unless all of the ingredients are soluble or otherwise homogeneously dispersed in water, co-solvents must be added in order to assure a homogeneous shampoo. Alcohols are frequently added as co-solvents in shampoos. Shampoos containing alcohol co-solvents are described in co-assigned U.S. Pat. No. 3,932,610. The alcohol may be monohydric such as ethyl alcohol, dihydric such as dipropylene glycol, or trihydric such as glycerine. Some of these alcohols, especially the monohydric alcohols, are disadvantageous because they irritate the skin, suppress foam and reduce viscosity. The dihydric and trihydric alcohols are disadvantageous mainly because of their high price. Glycerine may enhance foam somewhat but is extremely expensive.

It is also known to use saccharides in shampoos. Patents disclosing the use of saccharides in shampoos include U.S. Pat. Nos. 3,998,761, 3,988,438 and 2,237,629.

In order for deposition to occur, some attraction between the hair grooming agent and the hair must exist. The hair is negatively charged. Thus, effective hair grooming agents must be able to deposit on negatively charged surfaces.

Cationic grooming agents deposit on hair readily since they are strongly attracted to hair by the opposite charge. Since useful cationic grooming agents tend to have relatively high water-solubilities, most are soluble in water-based shampoo compositions.

Cationic hair grooming agents are typically cationic polymers and resins, such as cationic starch or cellulose derivatives. Some examples of cationic hair grooming agents are described in the following U.S. Patents:

U.S. Pat. No. 4,048,301
U.S. Pat. No. 4,009,256
U.S. Pat. No. 3,992,336
U.S. Pat. No. 3,990,991
U.S. Pat. No. 3,958,581

The hair grooming agent may also be a nonionic material. Various water-insoluble resinous, oily and waxy materials such as wood rosin, mineral oils and cocoamide constitute suitable nonionic hair grooming agents. These and other nonionic hair grooming agents are described in co-assigned U.S. Pat. Nos. 3,932,610, 3,950,510 and 3,533,955.

Nonionic hair grooming agents that have received considerable attention recently are the silicones. An article by Todd et al in "American Perfumer and Cosmetics", 86, 112 (1971) refers to the silky feel which silicones impart to hair. Silicones are also disclosed as hair grooming agents in shampoos in U.S. Pat. Nos. 4,087,518, 3,964,500, 3,950,510 and 2,826,551.

It is also known to increase the water-solubility of silicones. This may be done, for example, by providing a copolymer containing silicone and an alkylene glycol. Shampoos containing such solubilized silicones are described in U.S. Pat. Nos. 3,957,970 and 3,533,955.

It is frequently advantageous to provide a shampoo comprising both nonionic and cationic hair grooming agents. Such shampoos realize the separate benefits of both types of conditioners. Moreover, each charge type may actually enhance the benefits of the other.

Hair grooming agents may also be of the anionic type. In addition to containing the saccharide sorbitol, U.S. Pat. No. 3,988,438 (see above) describes a shampoo containing an alginate salt as a hair grooming agent.

Anionic hair grooming agents, however, deposit on negatively charged surfaces such as hair with difficulty due to electrostatic repulsion. Thus, most hair grooming agents are nonionic, cationic or mixtures thereof.

That is not to say that literature reports have not shown substantially of anionic hair grooming agents, and even detergents, to hair. Anionic grooming agents, however, deposit much less liberally from detergent systems than do cationic or nonionic agents and do not give the magnitude of effect of cationic or nonionic agents under comparable conditions.

Not all shampoos are freely pourable and homogeneous. Non-pourable, concentrated forms of shampoos such as gels and creme pastes have been known and used for some time. Such shampoos are added to only part of the hair and are worked into the rest of the hair after being diluted with water. Concentrated shampoos are unsatisfactory since homogeneous dispersion of the hair grooming agent throughout the hair is difficult. This incomplete dispersion leads to a disadvantageously uneven distribution of the hair grooming agent on the hair.

Two-phase shampoo systems have also been described; see, for example, U.S. Pat. No. 3,533,955. Typically, such shampoos contain a hair grooming agent in an oil phase and a detergent in an aqueous phase. Two-phase shampoos are applied to the hair in the form of temporary oil-in-water emulsions which must be formed by vigorously shaking the shampoo before use. These systems are disadvantageous because they are inherently non-homogeneous and, in addition, tend to have viscosities which are less than those preferred by consumers. Moreover, the use of two phase shampoos is inconvenient because of the requirement that they be shaken vigorously.

Despite considerable effort to improve shampoo systems, numerous problems still remain. One problem is providing a shampoo with copious form. Hair grooming agents such as silicone and co-solvents such as alcohol depress foam. Such foam suppression is disadvantageous since consumers prefer shampoos having good foam quality, i.e., having a high foam viscosity and volume.

The foaming of shampoos is caused by the presence of detergents. Thus, foam suppression due to the presence of certain hair grooming agents and co-solvents can be obviated by increasing the concentration of the detergent. Some detergents, however, can irritate the skin and the presence of high concentrations of detergents decreases the mildness of the shampoo.

Moreover, detergents lower the surface tension of extraneous materials on the hair, thereby promoting removal rather than deposition of hair grooming agents. Thus, high concentrations of detergents lower the amount of hair grooming agent deposited on the hair. As a result, increasing the concentration of the detergent enhances foam at the expense of mildness and conditioning.

Another problem, inherent in water-based homogeneous shampoos containing hair grooming agents, is that of obtaining the correct balance of stability. In the present context, stability refers to the maintenance of homogeneity. If a shampoo is too stable, the hair grooming agent will not readily deposit on the hair during the washing and rinsing processes. On the other hand, shampoos which are insufficiently stable will not remain homogeneous during storage.

Stability is a particularly serious problem in shampoos containing both a cationic hair grooming agent and an anionic detergent. This problem is discussed in U.S. Pat. No. 3,549,542. Apparently, a complex containing the cationic and anionic materials forms and settles out of the shampoo solution, dispersion, emulsion, or suspension. The instability of such shampoos can be countered by adding certain ampholytic and polar nonionic detergents and thickening agents. Special mixing techniques are also said to be helpful. Nevertheless, such methods add to the cost of manufacturing the shampoo and are otherwise not completely satisfactory.

Even shampoos which do not contain both an anionic detergent and cationic hair grooming agent are often unstable with time. The classical method for stabilizing such shampoos is by the addition of thickening agents. Thickening agents are, however, expensive and at the levels required to stabilize shampoos often decrease the pourability of the shampoo. This loss of pourability can make the removal of the shampoo from its container difficult and inconvenient. In addition, some of the shampoo may be lost since a large residue of the thickened shampoo tends to form on the walls of the container after the user has emptied the container as far as is practical.

The need continues to exist, therefore, for a homogeneous, freely pourable, stable, high foaming and mild shampoo containing effective cationic and/or nonionic hair grooming agents and an anionic detergent.

OBJECTS OF THE INVENTION

It is an object of the present invention to provide a substantially homogeneous, freely pourable, stable, water-based shampoo containing one or more nonionic and/or cationic hair grooming agents. It is a further object of the present invention to provide a shampoo which possesses high foam quality at relatively low concentrations of detergent. Still another object of the present invention is to provide a shampoo which is mild and also deposits a large amount of the hair grooming agent on the hair.

SUMMARY OF THE INVENTION

These and other objects of the present invention as will be understood by the following description, have been obtained by providing a freely pourable, stable, substantially homogeneous shampoo composition comprising:
 (a) about 15 to about 70% by weight of a water-miscible saccharide;
 (b) about 20 to about 75% by weight water;
 (c) about 0.1 to about 30% by weight of at least one nonionic or cationic hair grooming agent; and
 (d) about 3 to about 60% by weight of an anionic detergent,
the shampoo composition having a viscosity of about 400 to about 6000 CPS at 25° C.

DETAILED DESCRIPTION OF THE INVENTION

The shampoos of the present invention are stable, freely pourable from a suitable container and substantially homogeneous. In order to be freely pourable, the shampoo compositions should not be too highly viscous. The shampoos of the present invention have viscosities less than about 6000, preferably less than about 4500, and most preferably less than about 4000 cps as measured with a Brookfield viscometer.

By a substantially homogeneous shampoo is meant a shampoo composition in which all of the components are either dissolved, dispersed or suspended evenly throughout the shampoo. If, for example, the shampoo contains hair grooming components that are insoluble, these components will normally separate from the shampoo. In such cases, an undesirable product is obtained because the hair grooming aid is not uniformly dispersed throughout the mixture. As a result, different amounts will be dispensed depending on the concentration at various levels of the shampoo.

Shampoos containing suspensions of water-insoluble materials are stabilized by adjusting the viscosity of the system. In fact, a proper amount of thickness is desirable even in a shampoo in which all of the components are soluble. Shampoos which are not thickened may be too watery, in which case they tend to run off the hand when the shampoo is poured or to run off the hair during the shampooing operation. Shampoo which runs off the hair is wasted and may enter the eyes or mouth of the user. Thus, the shampoos of the present invention have viscosities of at least 400 cps, preferably at least 500 cps and most preferably at least 1,000 cps at 25° C. as measured with a Brookfield viscometer.

The present shampoos provide a rich, billowy high quality foam during use. Foam quality refers to foam volume and viscosity. Accordingly, the shampoos described and claimed herein provide superior foam volumes and, especially, foam viscosities.

It has surprisingly been found that the replacement of some of the water by certain saccharides in a shampoo stabilizes the shampoo and at the same time enhances the foam quality. Thus, the presence of a saccharide in a shampoo can increase the foam quality at a given concentration of detergents, or can maintain the same level of foam quality at a lower detergent concentration. At the same time, the saccharide thickens the shampoo and stabilizes the shampoo either by helping to dissolve the hair grooming agent or by keeping in suspension those hair grooming agents which are insoluble.

The enhancement of foam quality by the saccharides is surprisingly maintained even when the shampoo is diluted with a large proportion of water. Thus, in use, relatively little saccharide is present on the head. The mechanism for the enhancement of foam quality is not known.

In the present specification, the term saccharide includes mono-, di- and polysaccharide molecules as well as hydrogenation products and mixtures thereof. Suitable monosaccharides include glucose, dextrose, fructose and xylose. Preferably the monosaccharide is fructose or glucose. Suitable disaccharides include maltose and lactose.

Suitable polysaccharides include chains containing three or more units of glucose. While polysaccharides generally contain chains comprising mainly glucose, it is also possible for saccharides other than glucose to be present in the chain.

The upper limit of the number of units of a polysaccharide or the average number of units of a mixture of polysaccharides depends on the desired viscosity of the shampoo and on the concentration of saccharides in the shampoo at that viscosity. To achieve a given viscosity, the higher the concentration of saccharide the smaller the number of units per saccharide molecule. For example, a smaller amount of a twenty dextrose equivalent corn syrup than of a sixty dextrose equivalent corn syrup is required to achieve a given viscosity in a given shampoo system.

A further limitation of the number of units per saccharide molecule is the requirement that the saccharide be completely miscible with water. By miscible it is meant that a mixture of about 70 parts by weight saccharide and 30 parts by weight water will yield an essentially clear solution which is pourable at ambient temperature, i.e., about 30° F. or higher. Water miscibility decreases with increasing number of units per saccharide molecule.

It will frequently be desirable to employ hydrogenated saccharides equivalent in structure to the non-hydrogenated saccharides from which they were derived. This allows for greater shampoo stability with respect to color and aroma. The absence of a reducing group in hydrogenated saccharides enhances stability of the molecule to fermentation by micro-organisms and to such reactions as the browning reaction. Suitable hydrogenated saccharides include those derived from the hydrolysis of starches such as sorbitol and mixtures of sorbitol, maltitol, and the hydrogenated form of polysaccharides such as maltitriol and maltitetraol. Suitable methods for hydrogenating saccharides include those described in U.S. Pat. No. 3,329,507, DOS No. 2,008,865 and DOS No. 2,008,865.

It is normally very difficult to separate saccharides from one another. In commercial practice, therefore, a mixture of saccharides is used advantageously. Suitable mixtures of saccharides include syrups obtained by hydrolyzing carbohydrates. The hydrolysis may be catalyzed chemically or enzymatically or both as described in U.S. Pat. No. 3,329,507.

The carbohydrate hydrolyzed may be starch or cellulose. Starch hydrolyzates are particularly desirable because they are readily available, relatively inexpensive, relatively easy to prepare, and obtainable from a wide variety of sources such as corn, potato, wheat and rice.

A preferred saccharide for the present invention is corn or potato syrup. Due to availability, corn syrup is especially preferred in the United States while potato syrup is widely used in Europe.

The hydrolysis of the carbohydrate may be partial or complete. Complete hydrolysis leads to glucose. Partial hydrolysis leads to a mixture of saccharides. Such a mixture may contain monosaccharides, disaccharides and/or polysaccharides.

The saccharides of the present invention should have dextrose equivalents of about 20 to 100, preferably about 30 to 100 and most preferably about 30 to 70. Some suitable syrups for use in the present invention include corn syrups with about 20, 43 and 60 dextrose equivalent. Also useful is the so-called high fructose syrup made by the enzymatic conversion of glucose to fructose as well as the residues from various sugar and corn syrup refining processes.

It is not within the scope of the invention to include significant amounts of starch molecules which have not undergone hydrolytic degradation. Such starch materials build viscosity excessively even when present in relatively small amounts and do not provide the benefits of smaller saccharide units.

In addition, unhydrolyzed starch will not meet the miscibility requirement for saccharides useful in the present shampoos. However, it must be recognized that very low levels of such non-miscible material may be present since they cannot always be avoided. The small amounts present are such as not to interfere substantially, if at all, with the ability of the saccharide to meet the miscibility requirement.

The saccharides of the present invention are also clearly distinguishable from unhydrolyzed cellulose gums used to thicken some prior art shampoos. As is the case with starch, cellulosic gums fall outside the miscibility range cited above. In addition, cellulosic gums provide high thickening at low concentration. For example, a 2% solution of a cellulose gum such as sodium carboxymethylcellulose in water will yield an essentially non-pourable solution. A 2% solution of a saccharide of this invention, on the other hand, will change the viscosity of water only minimally. The resulting solution will flow readily.

The shampoos of the present invention contain about 15% to about 70%, preferably 20 to 60% and most preferably about 25 to about 50% by weight of a suitable saccharide. Concentrations of saccharides below the lower limit are outside the present invention since they do not provide sufficient foam viscosity enhancement or thickening. Concentrations of saccharides above the upper limit are undesirable because they may lead to shampoos which are too viscous and because they are economically disadvantageous. It is, however, not suggested that high levels will not provide the enhancement of foam viscosity realized with the lower levels. Levels higher than the upper limits claimed herein simply serve no purpose and only add to the expense of formulating the shampoo.

The water concentration of the shampoo is between about 20% and 75% by weight, preferably about 30% to about 60% by weight and most preferably about 40% to 60%. It is economically advantageous to use as much water as is possible. However, it is important for the purposes of this invention that the water content not exceed the maximum amounts claimed herein. Otherwise, the enhancement of form quality by the saccharide is insignificant.

The hair grooming agents of the present invention may be cationic or nonionic or mixtures of cationic and nonionic. Since hair generally contains a negative charge, anionic hair grooming agents are to be avoided. For example, the alginate salts described in U.S. Pat. No. 3,988,438 are unsuitable as hair grooming agents in the present invention.

Most soluble hair grooming agents are cationic. The amount of cationic grooming agents deposited on the hair depends on many factors. These include the nature of the particular cationic hair grooming agent used, its concentration in the shampoo, and the type and concentration of the detergent and other formulation aids. Less cationic material will deposit from a shampoo comprising an anionic surfactant than from one containing an amphoteric surfactant. This is probably because of complexation between the anionic surfactant and the cationic hair grooming aid, as discussed above.

Any cationic material capable of conditioning hair and suitable for use on human hair may be used in the shampoos of this invention. Some cationic hair grooming agents useful in the shampoos of the present invention include cationic polyamide polymers such as the low molecular weight adipic acid/diethylene-triamine polyamide and the copolymers of vinylpyrroldone and dimethylaminoethyl methacrylate quaternized with diethyl sulfate (Gafquat 755, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; the mineral acid salts of the amino-alkyl esters of homo- and copolymers of unsaturated carboxylic acids having from 3 to 5 carbon atoms described in U.S. Pat. No. 4,009,256; the long chain and polymeric quaternary ammonium salts described in U.S. Pat. No. 3,990,991; the quaternary nitrogen-containing cellulose ethers described in U.S. Pat. No. 3,962,418; and the copolymers and etherified cellulose and starch described in U.S. Pat. No. 3,958,581.

"Polymer JR", trademark of the Union Carbide Corp. is a preferred cationic grooming agent in the present shampoos, and has the structural formula:

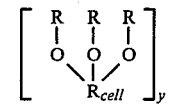

$R_{cell}$ in the formula represents the residue of an anhydroglucose unit ($C_6H_{10}O_5$). The R's may be the same or different and each R individually represents a substituent group of the formula given hereinbelow. The degree of polymerization is represented by y, which is an integer having a value of from about 50 to about 20,000, or more, and preferably from about 200 to about 5,000.

In the above structural formula each R individually represents a substituent group of the general formula:

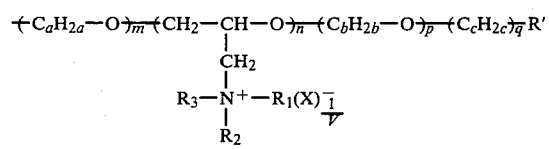

wherein:
a is an integer having a value of from 2 to 3;
b is an integer having a value of from 2 to 3;
c is an integer having a value of from 1 to 3;
m is an integer having a value of from zero to 10;
n is an integer having a value of from zero to 3;
p is an integer having a value of from zero to 10;
q is an integer having a value of from zero to 1;
R' is a member selected from the group consisting of

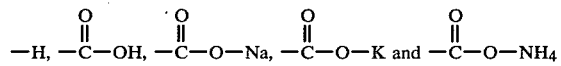

with the proviso that when q is zero then R' is —H; and V is the valence of X
$R_1$, $R_2$ and $R_3$, taken individually, represent a member selected from the group consisting of alkyl, aryl, aralkyl, alkaryl, cycloalkyl, alkoxyalkyl and alkoxyaryl radicals where each of $R_1$, $R_2$ and $R_3$ can contain up to 10 carbon atoms, with the proviso that when said member is an alkoxyalkyl radical there are at least 2 carbon atoms separating the oxygen atom from the nitrogen atom, and with the further proviso that the total number of carbon atoms in radicals represented $R_1$, $R_2$ and $R_3$ is from 3 to 12;
$R_1$, $R_2$ and $R_3$, taken together, represent, along with the nitrogen atom to which they are attached, a member selected from the group consisting of pyridine, -methylpyridine, 3,5-dimethylpyridine, 2,4,6- trimethylpyridine, N-methyl piperidine, N-ethyl piperidine, N-methyl morpholine and N-ethyl morpholine;

X is an anion such as chloride, bromide, iodide, sulfate, methylsulfate, sulfonate, nitrate, phosphate, acetate, etc., and V is an integer which is equal to the valence of X;

The average value of n per anhydroglucose unit is from about 0.01 to about 1 and preferably from about 0.1 to about 0.5; and The average value of m+n+p+q per anhydroglucose unit is from about 0.01 to about 4, more preferably from about 0.1 to about 2.5, and most preferably from about 0.8 to about 2.

Other preferred cationic hair grooming agents are cationic starch and cellulose derivatives such as the cationic guar gum derivatives offered by Celanese Corporation. The cationic guar gum derivatives are obtainable in various degrees of substitution, to give greater or lesser degrees of substantivity. They are designated in the dictionary of ingredients comiled by the Cosmetic, Toiletry and Fragrance Association (CTFA) as guar hydroxypropyltrimonium chloride. Degree of substitution in Jaguar C-17, for example, is given as 0.25–0.31.

The high molecular weight polymers sold under the trademark "Merquats" by Merck and Co., Inc., are cationic polymers which are also suitable for use in the present shampoos. Representative ones are Merquat 100, a highly charged cationic dimethyldiallylammonium chloride homopolymer, and Merquat 550, a highly charged cationic copolymer prepared with dimethyldiallylammonium chloride and acrylamide. These materials are designated in the CTFA dictionary as Quaternium-40 and Quaternium-41, respectively.

Insoluble hair grooming agents can be present in the shampoo composition as colloidal dispersions or emulsions, or as suspensions. These hair grooming agents may be cationic or nonionic. Most insoluble hair grooming agents are nonionic.

Suitable nonionic hair grooming agents are described in U.S. Pat. No. 3,932,610 and 3,533,955 and include silicones, resinous materials, waxy materials, and oily materials.

Silicones are the preferred insoluble hair grooming agents. The use of silicones in shampoos has been described in U.S. Pat. Nos. 2,826,551 and 3,964,500.

Silicones suitable for use in the present invention include polyalkyl or polyaryl siloxanes with the following structure:

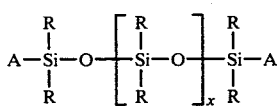

wherein R is alkyl or aryl, and x is an integer from about 100 to about 2,400. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the shampoo, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polydimethylphenylsiloxane. Polydimethylsiloxane is especially preferred.

Other silicones suitable for use in the present invention include the cyclic silicones. These materials are characterized by having structures such as:

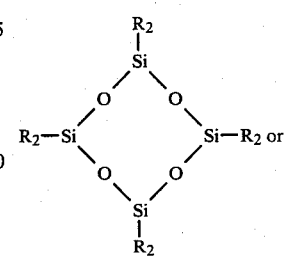

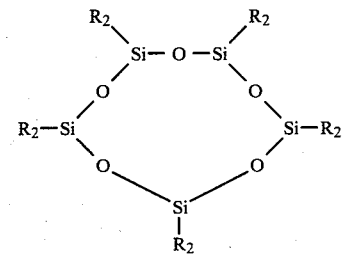

wherein R has the same meaning as in the structure of linear siloxanes.

The 8-membered and the 10-membered ring compounds wherein R represents methyl are generally available. These methylated cyclic silicones are votatile, and are thus present on the hair only temporarily. They are, therefore, especially preferred since they provide lubricity and other desirable qualities to the hair, as do their linear-chain counterparts, and then evaporate.

The silicone itself may have any practical viscosity as long as the shampoo composition containing the silicone has the desired viscosity. The preferred viscosity of the linear silicone is about 5 to about 300,000 centistokes at 25° C., preferably about 100 to about 200,000, and most preferably 10,000 to 100,000.

The cyclic silicones can be characterized generally, for example, by the following constants: specific gravity 0.960 at 25° C., viscosity about 5 centistokes at 25° C., and 98% volatile components. The 10-membered ring compound is less volatile than the 8-membered ring compound. They are insoluble in water. They are miscible with the linear chain silicones and can be used in conjunction therewith.

Suitable methods for preparing silicones are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

The silicones useful in the present shampoos may also be modified by adding polyethers as copolymers as is described in U.S. Pat. No. 3,957,970. Such copolymers tend to be more soluble than homopolymers of silicone.

Suitable resinous nonionic hair grooming agents useful in the present invention include wood rosins and their $C_1$–$C_6$ esters. The wood rosins or esters preferably have a softening point between about 96° C. to about 125° C. and a Gardner-Holt viscosity of between 20 and 40. Suitable wood rosin esters include polymerized dimerized rosins with softening points of 98° to 106° C. with acid numbers of at least 140, hydrogenated rosin with softening point of 69° to 80° C. and acid number of at least 158, and hydrogenated rosin methyl ester with boiling point between 350° to 380° C., preferably 360° C. and acid number of at least 7.

Other suitable resinous hair grooming agents include sucrose acetate isobutyrate, polyvinyl ethyl ether resin having a molecular weight from about 10,000 to 750,000, alkyl resins having a preferred molecular weight from about 10,000 to 50,000, polyketone resins having a preferred average molecular weight of from about 500 to 1,000, preferably 600 to 800, vinyl acetate resins having an average molecular weight of from about 8,000 to 15,000 and acrylic resin having an average molecular weight of from about 10,000 to 150,000. Mixtures of the above resins may also be used.

Suitable waxy materials include cocoamide, preferably having a melting point of about 80° to 90° C., ethoxylated lanolin containing about 5 to about 25 moles of ethylene oxide, stearyl amide preferably having a melting point of 95° to 110° C., ethoxylated higher fatty alcohols, preferably containing 14 to 30 carbon atoms and 2 to 4 moles of ethylene oxide, and the like. Mixtures of the above waxy materials may also be used.

Oily nonionic hair grooming agents may also be used. Suitable oily hair grooming agents include light mineral oils, lanolin alcohols, cetylated castor oil, fatty acid esters with isopropyl alcohol, mineral oil fractions, animal or vegetable oils such as linseed oil, castor oil, coconut oil and fractions thereof, and the like. Mixtures of the above liquid hair grooming agents may also be used.

A particularly preferred hair grooming agent system is a mixture of silicone and a cationic cellulose. The most preferred hair grooming agent is a mixture of polydimethylsiloxane and Polymer JR.

The hair grooming agent, or mixture of hair grooming agents, should be present in an amount from about 0.1 to 30 weight percent, preferably about 0.2 to 10 weight percent, and most preferably about 0.3 to 5 weight percent. At concentrations below the minimum concentration disclosed herein, the amount of the hair grooming agent that is deposited on the hair is insufficient to impart the desired conditioning to the hair. At concentration greater than the maximum concentration disclosed herein, the hair grooming agent tends to interfere with the detergent action of the surfactant system and to impart objectionable properties to the hair such as tackiness, greasiness, poor combing and/or flaking.

The identity of the detergents in the shampoo composition of the present invention is not critical as long as it provides a surfactant system capable of cleaning the hair and providing a rich form when present in a shampoo.

The surfactant system comprises one or more water-soluble surface-active agents, i.e., an anionic, nonionic, amphoteric surfactant, or a mixture thereof, which produces acceptable foam or whose foam is supplemented by a suds improver.

Anionic detergents are preferred since they provide richer, denser foams than other types of detergents at comparable concentrations. It is desirable for that reason that the surfactant system contain at least one anionic detergent. Suitable anionic detergents include sulfonated and sulfated alkyl, aralkyl and alkaryl anionic detergents; alkyl succinates; alkyl sulfosuccinates and N-alkoyl sarcosinates. Especially preferred are the sodium, magnesium, ammonium, and the mono-, di- and triethanolamine salts of alkyl and aralkyl sulfates as well as these salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic detergents include sodium lauryl sulfate, sodium oleyl succinate, ammonium lauryl sulfosuccinate, sodium lauryl ether sulfate, ammonium lauryl sulfate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine and ammonium lauryl sulfates. Sodium lauryl ether sulfate is also very suitable for use in the compositions of the invention.

Amphoteric or ampholytic detergents include N-lauryl-N'-carboxymethyl-N'-(2-hydroxyethyl)ethylenediamine, cocobetaine, and the Miranol compounds in U.S. Pat. Nos. 2,528,378 and 2,781,354. Other suitable amphoteric detergents include the quaternary cycloimidates, betaines, and sultaines disclosed in U.S. Pat. No. 3,964,500. The quaternary cycloimidates have the general structure:

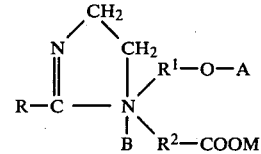

wherein
R is an aliphatic hydrocarbon radical having about 9 to about 17 carbon atoms,
$R^1$ and $R^2$ are each dependently
  a. a divalent alkylene radical having 1 to 4 carbon atoms,
  b. a hydroxy-substituted divalent alkylene radical having 2 to 4 carbon atoms,
  c. a divalent alkylene radical having 2–4 carbon atoms wherein said alkylene radical contains an ether or a keto linkage, and
  d. a hydroxy-substituted divalent alkylene radical having 2–4 carbon atoms wherein said alkylene radical contains an ether or a keto linkage,
M is a water-solubilizing cation,
A is
  a. M,
  b. —CH$_2$COOM
  c. —C$_2$H$_4$OCH$_2$COOM or
  d. —C$_2$H$_4$COOM, and
B is
  a. OH, b. $C_{12}H_{25}OSO_3-$, or c. $C_{12}H_{25}-C_6H_4-SO_3-$ Particularly preferred amphoteric surfactants are the substituted quaternary hydroxy cycloimidinic acid alkali metal alcoholates described in U.S. Pat. No. 2,528,378 and which have the generic structure:

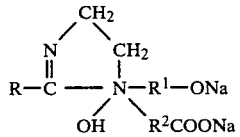

wherein R is an aliphatic hydrocarbon radical having about 9–17 carbon atoms, $R^1$ and $R^2$ represent divalent alkylene groups having 1 to 4 carbon atoms, and may be the same or different.

The most preferred of the amphoteric surfactants are the substituted quaternary hydroxy cycloimidinic acid alkali metal alkoxymethyl carboxylates described in U.S. Pat. No. 2,781,354, and which have the generic structure:

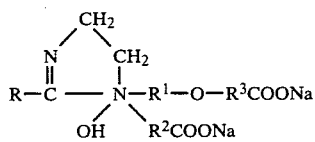

wherein R is an aliphatic hydrocarbon radical having about 9 to about 17 carbon atoms, $R^1$ and $R^2$ are as defined above, and $R^3$ is a divalent alkylene group having 1 to 2 carbon atoms.

A useful compound is one having the foregoing structure wherein R has 11 carbon atoms, $R^1$ has 2 carbon atoms and $R^2$ and $R^3$ each have 1 carbon atom.

The betaines may have the structure

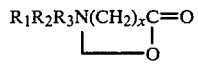

wherein $R_1$ is an alkyl group having about 12 to about 18 carbon atoms or a mixture thereof, $R_2$ and $R_3$ are independently lower alkyl groups having 1 to 3 carbon atoms, and N is an integer from 1 to 4. Specific betaines useful in the products of the invention are for example alpha-(tetradecyldimethylammonio)acetate, beta(-hexadecyldiethylammoninio)propionate, and gamma (dodecyldimethylammonio)butyrate.

The sultaines may have the structure

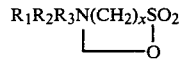

wherein $R_1$, $R_2$, $R_3$ and x are defined as above. Specific useful sultaines are for example 3-(dodecyldimethylammonio)propane-1-sulfonate, and 3-(tetradecyldimethylammonio)ethane-1-sulfonate.

Suitable nonionic detergents include fatty acid alkanolamides and the alkylene oxide (ethylene oxide and propylene oxide) condensates of a hydrophobic base such as long chain fatty alcohol or an alkylphenol. Typical of the fatty acid alkanolamides are those having a total of from 10 to 21 carbon atoms, such as lauric diethanolamide, coconut oil monoethanolamide and lauric isopropanolamide. The alkylene oxide condensates of long chain fatty alcohols include $C_{10}$ to $C_{21}$ fatty alcohols condensed with 3 to 20 moles of ethylene oxide, such as the ethylene oxide condensates of lauryl alcohol, myristyl alcohol and palmityl alcohol. The alkylene oxide condensates of alkylphenols include the alkylphenols having a $C_8$ to $C_{15}$ alkyl group condensed with 3 to 20 moles of ethylene oxide, such as the octylphenol-8 mole ethylene oxide condensate, and the nonylphenol-10 mole ethylene oxide condensate.

Other examples, well known to the art, may be found in the literature such as "Surface Active Agents" by Schwartz and Perry and "Surface Active Agents and Detergents" by Schwartz, Perry and Berch, both Interscience Publishers, New York, N.Y., the disclosures of which are incorporated herein.

Preferably the surfactant system is present in an amount from about 3 to about 60 percent, more preferably from about 7 to about 40 percent and most preferably from about 10 to about 30 percent by weight of the composition. Compositions containing lower amounts of surfactant than this do not clean the hair well and also give low foam volumes, while those containing greater amounts effect too great a dispersibility of the resin for deposition on the hair and introduce problems of eye irritancy.

Adjuvants may optionally be added to the shampoo composition. Thus, it is desirable to add an antibacterial agent to help preserve the system. Among the antibacterials that may be used are formaldehyde, imidazolidinyl urea, glutaraldehyde and other available products, e.g. Dowicil 200 offered by The Dow Chemical Company.

Other adjuvants may be added to inhibit darkening or other color deterioration of the shampoo. Ordinarily, such are not necessary. When the shampoo comprises certain reducing substances, as when it comprises corn syrup, it may be valuable to add an inhibitor of the so-called "browning reaction" which is well known in food technology. This reaction involves the free aldehydic groups of carbohydrates. It is markedly reduced by the addition of sulfite or bisulfite ions and by maintaining a relatively low pH. Thus, shampoos of this invention comprising corn syrup or other reducing sugars should preferably not be excessively alkaline if they are to have a good shelf life, the preferred pH being below about 8. Also, they will advantageously contain enough of a sulfite source as to provide 100 ppm or more sulfite or bisulfite as $SO_2$.

Further adjuvants include coloring agents and perfuming agents. Suitable coloring agents include FD&C and D&C dyes as well as non-toxic mineral pigments. Suitable perfuming agents include synthetic and naturally-occurring fragrance materials, such as various aldehydes, ketones, alcohols, and esters. These coloring and fragrancing materials are well known to those skilled in the art of formulating shampoos.

Soaps may be added to the surfactant systems in the shampoos. The soaps usable herein are well-known alkali metal, ammonium or substituted ammonium salts such as triethanolamine salts of natural or synthetic fatty acids having about 12 to 20 carbon atoms. The fatty acids may be saturated or unsaturated and may be derived from vegetable oils such as coconut oil, peanut oil, rapeseed oil, and corn oil or from animal sources such as tallow and lard. The alkali metals are preferably sodium or potassium. Ammonium ion may also be used.

Suitable soaps include sodium or triethanolamine laurate-myristate or sodium or triethanolamine oleate.

The shampoo compositions of the present invention may generally be prepared by blending the components followed by mixing them together until they are homogeneous. The methods are well known to those skilled in the art. Following preparation, the shampoos are stored and shipped in suitable containers such as glass or plastic bottles.

The shampoos of the present invention are freely pourable liquids which are expected to be used by the usual method of adding the shampoo to the hair, massaging the shampoo into the hair and removing the shampoo from the hair by rinsing with water.

The shampoos of the present invention have superior stabilities during storage and shipping. During the shampooing operation, the shampoos provide a rich and billowy lather. After the shampoo is rinsed from the hair, the hair is left in a clean and manageable condition.

In view of the unexpectedly superior foam enhancing and shampoo stabilizing properties of the saccharides used in the present invention, it is frequently neither necessary nor desirable that additional foam enhancers and shampoo thickeners be used. If for special purposes such foam enhancers and shampoo thickeners are desired, they may be added.

Additional thickeners are used if the desired shampoo viscosity is not obtained by the presence of the saccharide. In such cases, conventional thickeners may be used to increase the viscosity of the shampoo to the desired level. Suitable thickeners include carboxymethyl cellulose, methyl cellulose, hydroxypropyl cellulose, Carbopols (Goodrich Co.), vegetable gums, alginates and derivatives thereof, and latexes.

Various fatty acid amides may be used to obtain specific foam characteristics and to thicken the shampoo. Suitable amides include coconut fatty acid diethanolamide, lauric isopropanolamide and the like. These amides are usually not necessary, since the saccharide can be made to fulfill their function. They may also be undesirable because they add to the cost of the shampoo, depending on the relative costs of the amide and the saccharide and their levels of incorporation.

Having generally described the invention, a more complete understanding can be obtained by reference to certain specific examples which are provided herein for purposes of illustration only and are not intended to limit the invention unless otherwise specified.

EXAMPLES

A series of experiments were conducted to evaluate the effects of saccharides on the foam viscosity and volume of shampoos by replacing part of the water in the solvent by saccharides. A system was used which simulated human shampooing. The enhancement of foam viscosity as well as foam volume in the simulated system correlated well with control tests run in vivo by a beauty salon operator.

The principle of the simulated system was to dilute shampoo with water at approximately the dilution used in shampooing in vivo. The diluted shampoo was then whipped in a household food mixer under specific conditions. The volume of foam was then measured by determining the density of the foam generated and calculating the volume of the foam therefrom. The viscosity of the foam was measured by determining the time (in seconds) required to force the foam a specified distance through a capillary tube by air pressure produced by a plunger. The time required is a measure of the foam viscosity.

The apparatus for generating the foam consisted of a household food mixer equipped with a mixing bowl and two metal whisk-type beaters rotating in intersecting circles. The apparatus for measurement of foam viscosity consisted of an aluminum cup into which the foam was placed, a metal cap to fit over the cup, a capillary tube protruding from the cup, and a plunger which forced air into the cup to push the foam up the capillary tube. The cylindrical cup was 27 mm wide$\times$55 mm high. The tube was 30 cm long with 1 cm internal diameter. It had a calibration mark 25 mm from the top. An opening in the center of the metal cap accommodated the capillary tube, the bottom of which extended 20 mm below the bottom edge of the metal cap. A rubber grommet formed an airtight seal between the cap orifice and the wall. The metal cap also contained an air inlet to accept forced air from the plunger, which consisted of a metal cylindrical piston which moved freely through a glass barrel. The barrel was mounted vertically within an electric vibrating unit, which prevented the piston from stopping during its descent. To an outlet at the bottom of the barrel was affixed one end of plastic tubing. The other end was affixed to the air inlet on the metal cap.

Measurement of specific foam volume was accomplished through the use of a plastic Petri dish and a double pan torsion or a single pan electronic balance with readout capacity to the nearest 0.01 g.

The test solution was prepared as follows: Thirty ml of the test shampoo are diluted with 330 ml of tap water and mixed gently with a magnetic stirrer to avoid foaming. Fifty ml of this solution was transferred to the mixing bowl of the food mixer. The solution was then mixed at a predetermined speed (700 rpm) for exactly three minutes, by which time all of the solution was converted to foam. The mixer was stopped, and immediately 20 cc of foam were collected using a 20 cc glass syringe from which the shoulder and neck had been removed. The collected foam was transferred to the bottom half of the pre-weighed Petri dish. The top half was put into place over the bottom half and the dish was set aside for weighing. Another 20 cc of foam were quickly collected and transferred to the cylindrical cup. The piston of the plunger unit was raised to its maximum height and the vibrating device was activated. The metal cap with capillary tube was fitted tightly onto the cup. A finger was placed over the top of the capillary tube to prevent the piston from descending prematurely. An electric timer with readability to the nearest 0.1 sec. was used to measure the viscosity. The timer was activated at the exact moment at which the finger was removed from the top of the capillary tube. The piston moved downward, forcing air into the foam cup and pushing the foam up the tube. When the foam reached the calibration mark on the capillary tube, the time was noted. The elapsed time was taken as the foam viscosity.

The Petri dish containing the 20 cc of foam was weighed. The difference between the weight of the Petri dish alone and that of the Petri dish plus foam was the weight in grams of the foam. To determine the specific foam volume in cc/g, the volume of foam, 20 cc, was divided by the foam weight. Thus, foam volume, as given below, represents the volume of foam per unit weight of diluted shampoo.

A minimum of three replicates was used for each shampoo tested. Data were compared only within tests run as a series; series run at different times were not intercompared because of variations in such uncontrollable factors as mixed speed and operator variability. The precision in the foam volume measurments was ±4% and that in the foam viscosity measurements was ±7%.

EXAMPLE 1

In this experiment, the effect of adding saccharide on model shampoo systems was demonstrated. The following shampoos were formulated and evaluated by the in vitro foam test.

|  | Shampoo | | | |
|---|---|---|---|---|
|  | A | B | C | D |
|  | | Percent | | |
| Triethanolamine lauryl sulfate | 10.0 | 10.0 | 10.0 | 10.0 |
| Methocel E4M* | 0.2 | 0.2 | 0.2 | 0.2 |
| Coconut diethanolamide | — | 1.0 | — | 1.0 |
| Corn Syrup, 42 dextrose equivalent (80% solids)** | — | — | 40.00 | 40.00 |
| Water | to 100 | to 100 | to 100 | to 100 |
| Foam volume (cc/g) | 9.9 | 12.0 | 11.5 | 11.6 |
| Foam viscosity (sec) | 4.7 | 5.0 | 5.5 | 5.5 |

*Dow Chemical
**Staley 1300 corn syrup

The results showed that (1) as expected, addition of an amide to an alcohol sulfate model shampoo system increased foam volume appreciably while having a small, positive effect on foam viscosity, (2) the addition of sacharide to a detergent system without amide raised foam volume substantially and was even more effective in raising foam viscosity, and (3) addition of amide to the detergent/saccharide system provided no benefit.

EXAMPLE II

In this experiment, the effect of adding a foam depressing hair grooming agent was studied. Several formulations were prepared and evaluated by the in vitro foam test.

|  | Shampoo | | | | |
|---|---|---|---|---|---|
|  | A | B | C | D | E |
|  | | | Percent | | |
| Triethanolamine lauryl sulfate | 10.0 | 10.0 | 10.0 | 10.0 | 10.0 |
| Methocel E4M | 0.2 | 0.2 | 0.2 | 0.2 | 0.2 |
| Coconut diethanolamide | — | — | 1.0 | — | 1.0 |
| Corn syrup, 42 dextrose equivalent (80% solids) | — | — | — | 40.0 | 40.0 |
| Silicone, 60,000 centistrokes* | — | 2.0 | 2.0 | 2.0 | 2.0 |
| Water | to 100 | to 100 | to 100 | to 100 | to 100 |
| Foam volume (cc/g) | 9.9 | 8.9 | 9.2 | 10.8 | 9.9 |
| Foam viscosity (sec) | 4.7 | 4.4 | 4.3 | 5.7 | 4.7 |

*Viscasil, General Electric Co.

Several conclusions can be drawn from the data. (1) Addition of silicone to the simple detergent shampoo system depressed foam volume and to some extent, foam viscosity. (2) Addition to this system of a foam stabilizer, coconut diethanolamide, had little effect. (3) Addition of a saccharide markedly improved both foam volume and foam viscosity. And (4) further addition of coconut diethanolamide had only negative effects. These results further demonstrated the beneficial effects of saccharide in the current invention.

EXAMPLE III

In these experiments, the ability of the saccharide to enhance foam character even in the presence of alcohol was shown. Alcohol is of value for maintaining in solution some of the hair grooming agents of this invention. Two formulations were compared by the in vitro foam test. They were:

|  | Shampoo | | |
|---|---|---|---|
|  | A | B | C |
|  | | Percent | |
| Triethanolamine lauryl sulfate | 10.0 | 10.0 | 10.0 |
| Methocel E4M | 0.2 | 0.2 | 0.2 |
| Ethanol (95%) | 20.0 | 20.0 | 20.0 |
| Corn syrup, 42 dextrose equivalent (80% solids) | — | 40.0 | 30.0 |
| Water | to 100 | to 100 | to 100 |
| Foam volume (cc/g) | 9.8 | 10.8 | 10.4 |
| Foam viscosity (sec) | 4.66 | 4.83 | 5.10 |

Effects on foam volume as well as on foam viscosity were favorable in the presence of a substantial amount of alcohol.

EXAMPLE IV

In this test, another anionic surfactant was employed instead of triethanolamine lauryl sulfate, viz. alpha olefin sulfonate (AOS) (Sulframin AOS, Witco Chemical Corp.). The surfactant was tested at a level of 10%, active basis. The results were:

|  | Shampoo | | | |
|---|---|---|---|---|
|  | A | B | C | D |
|  | | Percent | | |
| AOS, active basis | 10.0 | 10.0 | 10.0 | 10.0 |
| Methocel E4M | 0.2 | 0.2 | 0.2 | 0.2 |
| Cocodiethanolamide | — | 1.0 | — | 1.0 |
| Corn syrup, 42 dextrose equivalent (80% solids) | — | — | 40.0 | 40.0 |
| Water | to 100 | to 100 | to 100 | to 100 |
| Foam volume (cc/g) | 9.9 | 10.7 | 9.9 | 11.4 |
| Foam viscosity (sec) | 4.13 | 4.60 | 4.86 | 5.13 |

From these data, it can be concluded that under the test conditions, the saccharide addition gave the same enhancement of foam viscosity to a model shampoo based on alpha olefin sulfonate as it did to a shampoo based on triethanolamine lauryl sulfate.

EXAMPLE V

The effect of adding the hair grooming agent, silicone, to the model shampoo systems of Example IV was studied. Formulations were made and tested as follows:

|  | Shampoo | | | | |
|---|---|---|---|---|---|
|  | A | B | C | D | E |
|  | | | Percent | | |
| AOS, active basis | 10.0 | 10.0 | 10.0 | 10.0 | 10.0 |
| Methocel E4M | 0.2 | 0.2 | 0.2 | 0.2 | 0.2 |
| Cocodiethanolamide | — | — | 1.0 | — | 1.0 |
| Corn syrup, 42 dextrose equivalent (80% solids) | — | — | — | 40.0 | 40.0 |
| Viscasil silicone, | — | 2.0 | 2.0 | 2.0 | 2.0 |

-continued

|  | Shampoo | | | | |
|---|---|---|---|---|---|
|  | A | B | C | D | E |
|  | | | Percent | | |
| 60,000 cps | | | | | |
| Water | to 100 | to 100 | to 100 | to 100 | to 100 |
| Foam volume (cc/g) | 9.9 | 9.5 | 9.0 | 10.2 | 10.6 |
| Foam viscosity (sec) | 4.1 | 4.6 | 4.2 | 5.3 | 5.7 |

It is readily seen that the silicone in this model system had a mixed effect, slightly depressing foam volume and slightly raising foam viscosity. Addition of the corn syrup, however, substantially increased foam viscosity without adversely affecting foam volume.

EXAMPLE VI

The effect of saccharide on an amphoteric model shampoo system was examined. The detergent used was Miranol 2 M CAS Modified, marketed by the Miranol Corporation. Four shampoo formulations were prepared, as indicated below. Formulations C and D were passed through a colloid mill to assure their homogeneity.

|  | Shampoo | | | |
|---|---|---|---|---|
|  | A | B | C | D |
|  | | Percent | | |
| Miranol 2MCAS Modified, active basis | 10.0 | 10.0 | 10.0 | 10.0 |
| Methocel E4M | 0.2 | 0.2 | 0.2 | 0.2 |
| Staley 1300 Corn Syrup, 42 dextrose equivalent (80% solids) | — | 40.0 | — | 40.0 |
| Viscasil Silicone, 60,000 cps | — | — | 2.0 | 2.0 |
| Water | to 100 | to 100 | to 100 | to 100 |
| Foam Volume (cc/g) | 13.4 | 12.9 | 12.4 | 13.7 |
| Foam Viscosity (sec) | 5.0 | 6.0 | 5.0 | 6.1 |

The data showed that addition of a saccharide markedly increased foam volume, whether or not the silicone was present. Addition of silicone to the model detergent system suppressed foam volume but not foam viscosity; foam volume was restored by the saccharide.

EXAMPLE VII

In this test, a very simple model shampoo was employed, viz., surfactant alone or with corn syrup. The results were:

|  | Shampoo | | | | | |
|---|---|---|---|---|---|---|
|  | A | B | C | D | E | F |
|  | | | Percent | | | |
| Triethanolamine lauryl sulfate, active basis | 4.0 | 4.0 | 4.0 | 12.0 | 12.0 | 12.0 |
| Corn syrup, 42 dextrose equivalent (80% solids) | — | 50.0 | 90.0 | — | 50.0 | 70.0 |
| Water to 100% | | | | | | |
| Foam volume (cc/g) | 9.6 | 10.3 | 10.3 | 10.3 | 10.1 | 10.8 |
| Foam viscosity (sec) | 4.4 | 5.4 | 6.7 | 4.7 | 5.9 | 7.1 |

The saccharide had little effect on foam volume, but markedly increased the foam viscosity regardless of concentration of the surfactant.

EXAMPLE VIII

Experiment VII was repeated, but triethanolamine lauryl ether sulfate (2 moles ethylene oxide) was substituted for the alkyl sulfate.

|  | Shampoo | | | | |
|---|---|---|---|---|---|
|  | A | B | C | D | E |
|  | | | Percent | | |
| Triethanolamine lauryl ether sulfate, active basis | 4.0 | 4.0 | 4.0 | 12.0 | 12.0 |
| Corn syrup, 42 dextrose equivalent (80% solids) | — | 50.0 | 87.7 | — | 63.0 |
| Water to 100% | | | | | |
| Foam volume (cc/g) | 9.4 | 9.8 | 10.0 | 8.7 | 9.3 |
| Foam viscosity (sec) | 3.8 | 5.2 | 5.7 | 4.0 | 5.2 |

The saccharide was effective in conjunction with a lauryl ether sulfate.

EXAMPLE IX

Since shampoos normally are used on oily hair, the foam test was conducted with the addition of 1% of an artificial sebum comprising fatty materials. The artificial sebum was added to the diluted shampoo. The results were:

Test 1. The model shampoo contained 12.0% triethanolamine lauryl sulfate, active basis. Foam volume was 11.0 and foam viscosity was 6.3 without saccharide. With 60% corn syrup (80% solids) the corresponding values were 11.9 and 8.6, respectively.

Test 2. Test 1 was repeated, but triethanolamine lauryl ether sulfate was substituted for triethanolamine lauryl sulfate, equal active weight basis. Foam volume and foam viscosity were 10.0 and 5.9, respectively, without saccharide, and 10.9 and 7.0, respectively, with the saccharide.

It was apparent that the saccharide beneficially affected foam viscosity even in the presence of fatty sebum.

EXAMPLE X

In this series of tests, shampoo formula B in Example I was prepared. Foam volume and foam viscosity were measured. Various saccharides, at different levels, were also added (in each instance adjusting the amount of water to compensate, if necessary). Foam volume and foam viscosity were again measured. The results were:

| ADDITION | FOAM VOLUME | FOAM VISCOSITY |
|---|---|---|
| 30% 42 Dextrose Equivalent Corn Syrup (80% solids) | 10.9 | 4.8 |
| 40% Sorbitol solution (70% solids) | 10.7 | 5.0 |
| 20% Sucrose | 10.5 | 4.9 |
| 30% Sucrose | 11.5 | 5.4 |
| 30% High Fructose Corn Syrup (80% solids) | 11.8 | 5.2 |
| 30% Hydrogenated Hydrolyzed Corn Starch (Lycasin) | 10.4 | 5.2 |
| 40% Non-crystallizing Sorbitol, containing about 10–12% di- and higher hydrogenated saccharides (70% solids) | 10.0 | 5.2 |
| No saccharide | 8.9 | 4.4 |

EXAMPLE XI

TABLE I

|  | 1 | 2 | 3 | 4 | 5 | 6 | 7 | 8 | 9 | 10 | 11 |
|---|---|---|---|---|---|---|---|---|---|---|---|
|  | PERCENT BY WEIGHT ||||||||||||
| Triethanolamine lauryl sulfate | 16.8 | 16.8 | 16.8 | 16.8 | 17.0 | 15.0 | 17.0 | 18.0 | 18.0 | 16.8 | 16.8 |
| Cocomonoethanolamide | 3.0 | 1.0 | 1.0 | 1.0 | — | — | 1.0 | — | — | 1.0 | 1.0 |
| Hydroxypropyl methylcellulose | 0.25 | 0.25 | 0.25 | 0.25 | 0.25 | 0.25 | 0.2 | 0.1 | 0.1 | 0.3 | 0.25 |
| Corn syrup, 42 dextrose equiv. (80%) | 20.5 | 20.5 | 21.0 | 21.0 | 21.0 | 30.0 | 22.0 | 40.0 | 40.0 | 21.0 | 20.5 |
| Dimethylpolysiloxane, | 1.0* | 2.0* | 1.0* | 1.0* | 1.0* | 1.0* | 2.0* | 1.0* | 1.0* | 1.0** | 1.0* |
| Alcohol, SDA 40 | 9.0 | 9.0 | 9.0 | 8.0 | 9.0 | 10.0 | 10.0 | 10.0 | 10.0 | 10.0 | 9.0 |
| Cationic cellulose (Polymer JR, Union Carbide) | 0.5 | 0.5 | — | — | 0.5 | 0.3 | 1.0 | 0.3 | — | 0.5 | 0.5 |
| Cationic Guar Gum (Jaguar C-17, Celanese) | — | — | 0.5 | 0.3 | — | — | — | — | 0.3 | — | — |
| Vinyl carboxy polymer (Carbopol 941, B.F. Goodrich) | 0.75 | 0.75 | 0.75 | 0.6 | 0.75 | 0.5 | 0.7 | 0.3 | 0.3 | 0.75 | 0.75 |
| Fragrance, color, sulfite preservative | q.s. | q.s. | q.s. | q.s. | q.s. | q.s. | q.s. | q.s. | q.s. | q.s. | q.s. |
| Acid and/or base To pH: | 6.5 | 6.5 | 6.7 | 6.7 | 7 | 6.7 | 6.5 | 7 | 6.5 | 6.5 | 6.5 |
| Water To: | 100 | 100 | 100 | 100 | 100 | 100 | 100 | 100 | 100 | 100 | 100 |

*60,000 centistokes, General Electric Co.
**Volatile silicone, General Electric Co.

TABLE II

|  | 12 | 13 | 14 | 15 | 16 | 17 | 18 |
|---|---|---|---|---|---|---|---|
|  | PERCENT BY WEIGHT |||||||
| Surface Active Agent | Sodium lauryl ether sulfate 2 EO | Ammonium lauryl sulfate | Sodium lauryl sulfate | Sodium lauryl sulfate | Triethanolamine lauryl sulfate & Miranol 2MCS Mod. (1:1, active basis) | Miranol H2M conc.* & lauryl ether sulfate** (2:1, active basis | Triethanolamine lauryl sulfate |
|  | 17.0 | 16.8 | 14.0 | 15.0 | 20.0 | 20.0 | 17.0 |
| Foaming Aid | Cocomonoethanal amide | Lauric isopropanolamide | — | Cocomonoethanolamide | Lauric isopropanolamide | — | Lauric isopropanolamide |
|  | 1.0 | 1.0 | — | 1.5 | 1.5 | — | 1.0 |
| Saccharide | High fructose corn syrup, 80% | Corn syrup, 80%, 42 DE | Sorbitol, 70% | Hydrogenated 42 DE Corn Syrup | Sorbitol, 70% | Corn Syrup, 80%, 42 DE | Sucrose |
|  | 25.0 | 15.0 | 30.0 | 30.0 | 35.0 | 30.0 | 20.0 |
| Cationic Additive | — | — | Merquat, Merck & Co. | Polymer JR | Polymer JR | Catrex, National Starch | Polymer JR |
|  | — | — | 2.0 (active) | 0.7 | 0.3 | 1.0 (active) | 0.5 |
| Hair Grooming Agent | Methyl hydrogenated rosinate | Methyl hydrogenated rosinate | Silicone, 60,000 csk | Silicone, 1,000 csk | Silicone, 60,000 csk | Silicone, 60,000 csk | Light mineral Oil |
|  | 5.0 | 5.0 | 1.0 | 2.0 | 1.0 | 1.5 | 3.0 |
| Thickener | Hydroxypropyl methylcellulose | Hydroxypropyl methylcellulose | Methylcellulose | Hydroxypropyl methylcellulose | Xanthan Gum | Hydroxypropyl methylcellulose | Hydroxypropyl methylcellulose |
|  | 0.75 | 0.75 | 0.5 | 0.75 | 0.3 | 0.5 | 0.5 |
| Preservative | Formaldehyde 0.1% & NaHSO3 0.3% | Sodium formaldehyde bisulfite | Dowicil 200 Dow Chemical Company | Formaldehyde | Formaldehyde | Dowicil 200 | Sodium formaldehyde bisulfite |
|  | 0.3 | 0.25 | 0.1 | 0.1 | 0.1 | 0.1 | 0.25 |
| Other Additives | Ethylenediamine tetraacetate | Cododiethanolamide | — | Ethylenediamine tetraacetate | Ethylenediamine tetraacetate | — | — |
|  | 0.1 | 1.0 | — | 0.1 | 0.1 | — | — |
|  | — | SDA 40 Alcohol | SDA 40 Alcohol | SDA 40 Alcohol | — | SDA 40 Alcohol | SDA 40 Alcohol |
|  | — | 10.0 | 10.0 | 8.0 | — | 10.0 | 10.0 |
| Acid or alkali to pH 7; color, fragrance, water to | 100% | 100% | 100% | 100% | 100% | 100% | 100% |

*Miranol Chemical Co.,
**Maprofix ES, Onyx Chemical Co.

A series of shampoo was prepared comprising various surfactant and hair grooming ingredients and sources of saccharide. These are described in the following Tables. All of the shampoos yielded excellent foam when used for washing hair in the normal fashion.

Having now fully described the invention, it will be apparent to one of ordinary skill in the art that many changes and modifications can be made thereto without departing from the spirit or scope of the invention as set forth herein.

What is claimed is:

1. A freely pourable, substantially homogeneous shampoo composition comprising:
   (a) about 15 to about 70% by weight of a water-miscible saccharide;
   (b) about 20 to about 75% by weight water;
   (c) about 0.1 to about 30% by weight of at least one nonionic or cationic hair grooming agent; and
   (d) about 3 to about 60% by weight of an anionic or amphoteric detergent,
the shampoo composition having a viscosity of about 400 to about 6,000 cps at 25° C.

2. The shampoo composition of claim 1 wherein the viscosity is about 500 to about 4,500 cps at 25° C.

3. The shampoo composition of claim 1 wherein the viscosity is about 1,000 to about 4,000 cps at 25° C.

4. The shampoo composition of claim 1 wherein the saccharide is a mixture of monosaccharide, disaccharide and polysaccharide.

5. The shampoo composition of claim 1 wherein the saccharide is a monosaccharide.

6. The shampoo composition of claim 5 wherein the monosaccharide is selected from the group consisting of glucose and fructose.

7. The shampoo composition of claim 1 wherein the concentration of saccharide in the shampoo is between 20 and 60 weight percent.

8. The shampoo composition of claim 1 wherein the concentration of saccharide in the shampoo is between about 25 and 50 weight percent.

9. The shampoo composition of claim 1 wherein the saccharide is hydrogenated.

10. The shampoo composition of claim 1 wherein the saccharide is prepared by hydrolyzing carbohydrate.

11. The shampoo composition of claim 10 wherein the carbohydrate comprises starch.

12. The shampoo composition of claim 10 wherein the starch comprises corn starch or potato starch.

13. The shampoo composition of claim 11 wherein the starch comprises corn starch.

14. The shampoo composition of claim 11 wherein the saccharide has a dextrose equivalent of about 20 to 100.

15. The shampoo composition of claim 1 wherein the saccharide has a dextrose equivalent of about 30 to 70.

16. The shampoo composition of claim 1 wherein the water comprises about 30 to 60% by weight of the total composition.

17. The shampoo composition of claim 1 wherein the water comprises about 40 to 60% by weight of the total composition.

18. The shampoo composition of claim 1 further comprising an amount of a monohydric alcohol, a dihydric alcohol, or a trihydric alcohol, said amount being effective to assist the dispersion or dissolution of the hair grooming agent.

19. The shampoo composition of claim 18 wherein the monohydric alcohol, dihydric alcohol, or trihydric alcohol is ethyl alcohol, propylene glycol or glycerine.

20. The shampoo composition of claim 1 wherein the hair grooming agent is cationic.

21. The shampoo composition of claim 20 wherein the cationic hair grooming agent is a cationic cellulose derivative.

22. The shampoo composition of claim 21 wherein the cationic cellulose derivative is Polymer JR.

23. The shampoo composition of claim 20 wherein the cationic hair grooming agent is cationic guar gum.

24. The shampoo composition of claim 1 wherein the hair grooming agent is insoluble in the shampoo.

25. The shampoo composition of claim 1 wherein the hair grooming agent is soluble in the shampoo.

26. The shampoo composition of claim 1 wherein the hair grooming agent is nonionic.

27. The shampoo composition of claim 26 wherein the nonionic hair grooming agent comprises wood rosin.

28. The shampoo composition of claim 27 wherein the wood rosin is in the form of its $C_1$-$C_6$ ester.

29. The shampoo composition of claim 26 wherein the hair grooming agent is selected from the group consising of sucrose acetate isobutyrate, polyvinyl ethyl ether resin having amolecular weight from about 10,000 to 75,000, alkyl resins having a molecular weight from 10,000 to about 50,000, polyketone resins having an average molecular weight from about 500 to 1,000, vinyl acetate resins having an average molecular wweight of from about 8,000 to 15,000, acrylic resin having an average molecular weight of from about 10,000 and 150,000, and mixtures thereof.

30. The shampoo composition of claim 26 wherein the hair grooming agent is selected from the group consisting of cocoamide, ethoxylated lanolin containing about 5 to about 25 moles of ethylene oxide, stearyl amide having a melting point of 95° to 110° C., ethoxylated higher fatty alcohols containing 14 to 30 carbon atoms and 2 to 4 moles of ethylene oxide and mixtures thereof.

31. The shampoo composition of claim 26 wherein the hair grooming agent is selected from the group consisting of lanolin alcohols having a viscosity of 10 to 30 cps at 20° C., cetylated castor oil having a saponification value of about 144 to 150, mineral oil having a saybolt viscosity of about 50 to about 367 and mixtures thereof.

32. The shampoo composition of claim 1 wherein the hair grooming agent comprises a silicone.

33. The shampoo composition of claim 32 wherein the silicone has the formula

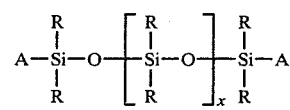

wherein A represents methyl, methoxy, ethoxy, propoxy, or aryloxy and R represents methyl, ethyl, propyl or phenyl and x is an integer from about 100 to about 2,400.

34. The shampoo composition of claim 33 wherein R represents methyl.

35. The shampoo composition of claim 32 wherein the silicone has the structure

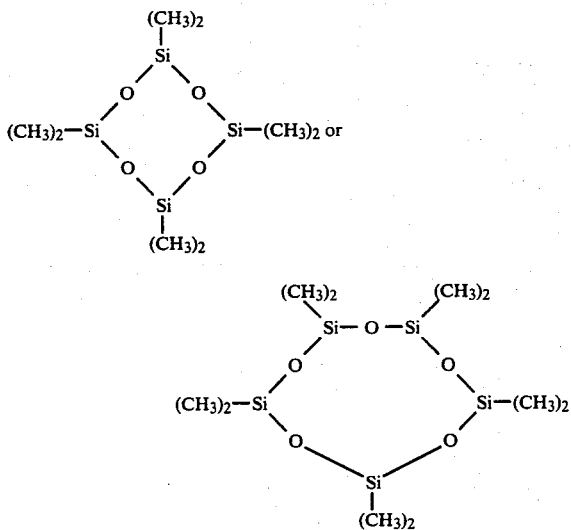

36. The shampoo composition of claim 32 wherein the silicone has a viscosity of 5 to 300,000 cps at 25° C.

37. The shampoo composition of claim 32 wherein the silicone has a viscosity of 100 to 200,000 centistokes at 25° C.

38. The shampoo composition of claim 32 wherein the silicone has a viscosity of 10,000 to 100,000 centistokes at 25° C.

39. The shampoo composition of claim 1 wherein the hair grooming agent comprises a cationic cellulose and a silicone.

40. The shampoo composition of claim 1 wherein the concentration of the hair grooming agent is 0.1 to 30 weight percent.

41. The shampoo composition of claim 1 wherein the concentration of the hair grooming agent is 0.2 to 10 weight percent.

42. The shampoo composition of claim 1 wherein the concentration of the hair grooming agent is from 0.3 to 5 weight percent.

43. The shampoo composition of claim 1 wherein the detergent is an alkyl or aralkyl sulfate or an alkyl or aralkyl sulfate ether.

44. The shampoo composition of claim 1 wherein the detergent is an alkaryl sulfonate.

45. The shampoo composition of claim 43 wherein the detergent is selected from the group consisting of sodium lauryl sulfate, sodium lauryl ether sulfate, monoethanolamine lauryl sulfate, triethanolamine lauryl sulfate, ammonium lauryl sulfate, and mixtures thereof.

46. The shampoo composition of claim 1 wherein the concentration of anionic detergent is about 7 to about 40 percent by weight.

47. The shampoo composition of claim 1 wherein the concentration of anionic detergent is about 10 to about 30 percent by weight.

48. The shampoo composition of claim 1 further comprising an amphoteric or nonionic detergent.

49. A freely pourable substantially homogeneous shampoo composition comprising
 (a) 15 to about 70% by weight of corn syrup;
 (b) about 20 to about 75 percent by weight water;
 (c) about 0.1 to about 30 percent by weight of a hair grooming agent comprising a silicone;
 (d) about 3 to about 60 percent by weight of an anionic detergent;
wherein the viscosity of the shampoo composition is about 400 to 6000 cps at 25° C.

50. The shampoo composition of claim 49 wherein the hair grooming agent further comprises polymer JR.

51. The shampoo composition of claim 49 wherein the hair grooming agent further comprises cationic guar gum.

52. The shampoo composition of claim 49 wherein the silicone comprises polydimethylsiloxane.

53. A freely pourable substantially homogeneous shampoo composition comprising:
 (a) about 17% by weight of triethanolamine lauryl sulfate;
 (b) about 21% by weight of corn syrup;
 (c) about 17% by weight of polydimethylsiloxane;
 (d) about 0.5% by weight of a cationic cellulose; and
 (e) about 50% water.

54. The shampoo of claim 53 wherein the corn syrup has a dextrose equivalent of about 42.

55. The shampoo of claim 53 wherein the polydimethylsiloxane has a viscosity of about 60,000 centistokes at 25° C.

* * * * *

UNITED STATES PATENT AND TRADEMARK OFFICE
CERTIFICATE OF CORRECTION

PATENT NO. : 4,364,837
DATED : December 21, 1982
INVENTOR(S) : Morton Pader

It is certified that error appears in the above—identified patent and that said Letters Patent is hereby corrected as shown below:

Column 24, line 20: "having amolecular weight" should read
-- having a molecular weight --.

Column 24, line 26: "molecular wweight" should read
-- molecular weight --.

Signed and Sealed this

Sixteenth Day of August 1983

[SEAL]

Attest:

GERALD J. MOSSINGHOFF

Attesting Officer     Commissioner of Patents and Trademarks